US010488388B2

(12) United States Patent
Van Mechelen et al.

(10) Patent No.: US 10,488,388 B2
(45) Date of Patent: Nov. 26, 2019

(54) HYDROGEN SENSOR, HYDROGEN DETECTION SYSTEM EMPLOYING THE SAME, AND ELECTRICAL DEVICE WITH A HYDROGEN DETECTION SYSTEM

(71) Applicant: ABB Schweiz AG, Baden (CH)

(72) Inventors: Jacobus Lodevicus Martinus Van Mechelen, Regensdorf (CH); Barbara Panella, Wettingen (CH); Mercedes Victoria Garcia, LW Delft (NL); Ruud Johannes Westerwaal, BX Barsingerhorn (NL); Bernard Dam, GE The Hague (NL)

(73) Assignee: ABB Schweiz AG, Baden (CH)

( * ) Notice: Subject to any disclaimer, the term of this patent is extended or adjusted under 35 U.S.C. 154(b) by 555 days.

(21) Appl. No.: 14/828,641

(22) Filed: Aug. 18, 2015

(65) Prior Publication Data

US 2016/0054286 A1 Feb. 25, 2016

(30) Foreign Application Priority Data

Aug. 19, 2014 (EP) .................................... 14181427

(51) Int. Cl.
*G01N 33/28* (2006.01)
*G01N 21/77* (2006.01)
*G01N 21/75* (2006.01)

(52) U.S. Cl.
CPC ..... *G01N 33/2841* (2013.01); *G01N 21/7703* (2013.01); *G01N 2021/772* (2013.01);
(Continued)

(58) Field of Classification Search
CPC .......... G01N 33/2841; G01N 33/2835; G01N 33/28; G01N 33/26; G01N 21/7703; G01N 21/77; G01N 21/75; Y10T 436/22
(Continued)

(56) References Cited

U.S. PATENT DOCUMENTS 5,039,492 A * 8/1991 Saaski ................... G01N 21/77
356/412
5,783,152 A * 7/1998 Nave ................... G01N 21/783
422/82.06
(Continued)

FOREIGN PATENT DOCUMENTS

| EP | 2559778 A1 | 2/2013 |
| WO | 9636084 A1 | 11/1996 |
| WO | 2007049965 A1 | 5/2007 |

OTHER PUBLICATIONS

European Search Report Application No. EP 14 18 1427 Completed: Jan. 28, 2015 3 pages.
(Continued)

*Primary Examiner* — Christine T Mui
(74) *Attorney, Agent, or Firm* — Whitmyer IP Group LLC (57) ABSTRACT

An optical sensor for detecting hydrogen in a fluid in physical contact with the sensor is provided. The sensor includes an optical fiber, wherein an end portion of the optical fiber is coated with a multilayer including: a sensing layer, including a film of an alloy, the alloy including Mg, Ni, and M, wherein M is at least one of Zr, Ta, and Hf, and wherein the alloy has the composition $Mg_xNi_yM_z$, and wherein x is from 40 to 60, y is from 10 to 40, and z is from 10 to 40, and a catalyst layer including Pd. Further, a detection system for hydrogen, including such an optical sensor, and an electrical device having such a detection system are provided.

15 Claims, 5 Drawing Sheets

(52) U.S. Cl.
CPC ............... *G01N 2021/7773* (2013.01); *G01N 2201/088* (2013.01)

(58) Field of Classification Search
USPC ...................................... 436/144; 422/82.06
See application file for complete search history.

(56) References Cited

U.S. PATENT DOCUMENTS

2002/0089732 A1   7/2002   Ouwerkerk et al.
2009/0283421 A1   11/2009  Farangis et al.

OTHER PUBLICATIONS

Slaman, et al: "Fiber optic hydrogen detectors containing Mg-based metal hydrides", Sensors and Actuators B: Chemical: International Journal Devoted to Research and Development of Physical and Chemical Transducers, Elsevier S.A, CH, vol . 123, No. I, Mar. 30, 2007, pp. 538-545, p. 539, left-hand column, last paragraph, right-hand column, paragraph 1, figure 1, p. 540, left-hand column, paragraph 2.

Mak T et al: 11 0ptical fiber sensor for the continuous monitoring of hydrogen in oil 11, Sensors and Actuators B: Chemical: International Journal Devoted to Research and Development of Physical and Chemical Transducers, vol. 190, Sep. 26, 2013, pp. 982-989, figures 1,2,7, p. 983, right-hand column, line 1, p. 984, left-hand column, line 3.

Slaman M et al: "Optical hydrogen sensors based on metal-hydrides", Photonic Applications for Aerospace, Transportation, and Harsh Environment III, SPIE, 1000 20th St. Bellingham WA 98225-6705 USA, vol. 8368, No. I, May 11, 2012 , pp. 1-8.

\* cited by examiner

HYDROGEN SENSOR, HYDROGEN DETECTION SYSTEM EMPLOYING THE SAME, AND ELECTRICAL DEVICE WITH A HYDROGEN DETECTION SYSTEM

FIELD OF THE INVENTION

Aspects of the present disclosure relate to a hydrogen sensor, a hydrogen detection system employing the same, and to an electrical device including such a detection system. In particular, aspects relate to a hydrogen sensor and a hydrogen detection system with such a sensor for liquid-filled electrical equipment, and more particularly to oil-filled electrical transformers having such hydrogen detection systems and hydrogen sensors.

BACKGROUND OF THE INVENTION

Insulation-liquid-filled electrical equipment, such as oil-filled shunt reactors, bushings, and especially transformers such as power and distribution transformers, are filled with insulation liquid, in particular oil, for cooling and electrical insulation purposes. Faults inside the electrical equipment as well as degradation of the insulation liquid and of other insulation components such as insulation paper provided within the electrical equipment can form decomposition gasses which mainly dissolve into the liquid. This is valid for equipment employing both mineral oil and oil from natural sources.

It is important to detect such faults, errors and degradations early, since especially transformers are important components of the electrical grid, and their failure can be very costly. Hence, a transformer is supposed to operate continuously and as error-free as possible over many years or even decades.

The quantity and composition of the decomposition gases is dependent on the underlying defect: A large fault with high energy content, such as rapid overheating or arcing, causes large amounts of gas to be produced in a short period of time, whereas the amount of gas produced by a small fault may be relatively smaller. Also, the relative concentrations of the different gasses dissolved might indicate the specific type of fault. Thus, if the nature and amount of individual gases dissolved in the insulation liquid are known, the occurrence of a change of the concentration of a specific gas in the oil can be used to identify an electrical fault in the equipment. It is known that one of the most important indicators for electrical failure in oil insulated transformers is the occurrence of hydrogen gas dissolved in the oil, which is for example produced at a faulty portion of an insulation of a winding of the transformer by thermal or electrical decomposition of the oil. For this reason, it is desirable that such errors, which may eventually cause complete failure of the transformer, can be detected as early as possible by identifying a rise in hydrogen concentration. This should ideally be possible at a stage when appropriate countermeasures may still be taken before serious and potentially costly malfunction occurs.

At a very early stage of such an electrical fault, only a very small amount of hydrogen gas may be produced, which dissolves in the oil and thus a concentration of dissolved hydrogen builds up in the oil over a longer period of time—whereby the hydrogen concentration in the oil may, at least during an early phase of the failure, even be below a threshold at which it can be detected with most known detection methods.

Most modern electrical transformers in power grids are still not equipped with on-line or real-time monitoring devices for such gasses. In order to control and evaluate the health of these transformers, an oil sample from the insulating oil bath is periodically taken and sent to qualified laboratories where the dissolved gases and other oil properties are measured. This monitoring method is time consuming, lacks continuity, has the risk of human error and is highly priced. Even if this costly method is carried out more frequently, there are several possible sources for error in the process, for example changes in the chemical and physical properties of the probe during the transport between the point in time when the probe is drawn, and the moment when the gas content is actually determined in a laboratory. Also, this method does not provide any information on where a fault occurred in the transformer. Thus, this method shall be of no further interest here, even though it is still widely used.

On the other hand, in online-methods the gas concentration in the insulation liquid is monitored directly and (quasi-)continuously. For this purpose, monitoring systems exist, sometimes built-in, for measuring hydrogen in transformer oil. These systems are based on different sensing techniques. They include, for example, semiconductor sensors, thermal-conductivity analyzers, pellistors, and fuel cell sensors, amongst others. These sensing techniques usually require a complicated gas separation system that adds complexity and cost to the sensor design and calibration. Thus, these devices are generally cumbersome and expensive. Additionally, some of these monitoring techniques suffer from cross-sensitivity towards other gases present in the oil, which additionally makes the results less reliable.

Therefore, even advanced transformers, i.e. those equipped with a dedicated on-line gas monitoring system, are often still additionally and periodically verified with expensive laboratory tests to reassure the accuracy of the on-line gas monitoring system. Therefore, a quantitative, reliable, cheap and continuous hydrogen detection system employing a sensor would be ideal for monitoring hydrogen concentration in the insulating oil in order to be able to detect faults at a stage as early as possible. This implies that a health status of the transformer can be monitored online or even from a remote location.

There have been proposals for such on-line hydrogen monitoring devices which include thin film based fiber optic sensors, wherein a sensing material changes its optical properties upon an exposure to hydrogen dissolved in the oil. One such system for detecting hydrogen gas is described as an optical switching device in WO 2007 049965 A1.

Another proposal is provided in "Optical fiber sensor for the continuous monitoring of hydrogen in oil" by T. Mak, R. J. Westerwaal, M. Slaman, H. Schreuders, A. W. van Vugt, M. Victoria, C. Boelsma, B. Dam, in: Sensors and Actuators B 190 (2014) 982-989. Thereby, the proposed optical sensors include a sensitive film comprising, for example, an alloy of Mg and Ti, capped with a Pd-containing layer.

However, such known configurations leave great room for improvement. Firstly, the sensitivity of some of these sensors has, which may even be intended, a switch-type characteristic in the temperature regimes of interest. That is, these optical sensors fundamentally change their optical properties, namely their reflectance, when a threshold value of the supervised hydrogen concentration in the oil is reached. This means that a hydrogen detection system with such a sensor can and will only indicate if a certain threshold concentration of hydrogen has been reached or not. It can thus typically not detect or indicate that a slow rise of the hydrogen concentration occurs over a longer time period such as hours, days or even months, which might, however, be regarded as an indication for a slowly developing fault. Thus, it does not indicate the actual hydrogen concentration in the transformer oil, but only that a threshold value for the gas concentration has been reached or exceeded.

Other optical sensors do exhibit a continuous change of their optical properties with growing hydrogen concentrations in the oil, however they lack sensitivity in certain temperature and hydrogen concentration regimes which would be desirable for enabling monitoring the hydrogen concentration at a broad range of possible operating conditions of transformers. For example, the hydrogen sensor as used by Mak et al. (2014) can measure hydrogen concentrations continuously from 5 ppm to 1,500 ppm, however only above an operating temperature of 80° C. of the sensor. This is, however, higher than the standard oil temperature in most transformer types. At lower operating temperatures, which are much more significant for standard transformer operation, the effective measurement ranges for hydrogen concentrations are much smaller (and the sensitivity lower) with the known technology, so that it is improvable for the detection of transformer faults. In addition, often these metal-hydride systems do not show a reproducible optical behavior upon hydrogen cycling as required, which results in an instable response of the sensor over time.

In view of the above and other factors, there is a need for the present invention.

SUMMARY OF THE INVENTION

In view of the above, the invention provides an optical sensor according and a detection system.

According to an aspect, an optical sensor for detecting hydrogen in a fluid in physical contact with the sensor is provided. The optical sensor comprises an optical fiber, wherein an end portion of the optical fiber is coated with a multilayer which comprises: a sensing layer, comprising a film of an alloy, the alloy comprising Mg, Ni, and M, wherein M is at least one of Zr, Ta, and Hf, and wherein the alloy has the composition $Mg_xNi_yM_z$, and wherein x is from 40 to 60, y is from 10 to 40, and z is from 10 to 40, and a catalyst layer comprising Pd.

According to another aspect, a detection system for hydrogen in fluids is provided, which comprises an optical fiber, wherein an end portion of the optical fiber is coated with a multilayer which comprises: a sensing layer, comprising a film of an alloy, the alloy comprising Mg, Ni, and M, wherein M is at least one of Zr, Ta, and Hf, and wherein the alloy has the composition $Mg_xNi_yM_z$, and wherein x is from 40 to 60, y is from 10 to 40, and z is from 10 to 40, and a catalyst layer comprising Pd, a temperature sensor, a light source, a light detection device, and a control unit, wherein light from the light source is coupled into the optical sensor, light reflected by the multilayer of the optical sensor is detected by the light detection device, and wherein the control unit processes an output signal of the light detection device, determines a hydrogen concentration, and delivers a respective signal.

According to a further aspect, a device for electric power generation, transmission, or distribution is provided. It comprises an oil volume and a detection system for hydrogen in fluids, comprising an optical sensor which comprises an optical fiber, wherein an end portion of the optical fiber is coated with a multilayer comprising: a sensing layer, comprising a film of an alloy, the alloy comprising Mg, Ni, and M, wherein M is at least one of Zr, Ta, and Hf, and wherein the alloy has the composition $Mg_xNi_yM_z$, and wherein x is from 40 to 60, y is from 10 to 40, and z is from 10 to 40, a catalyst layer comprising Pd, a temperature sensor, a light source, a light detection device, and a control unit, wherein light from the light source is coupled into the optical sensor, light reflected by the multilayer of the optical sensor is detected by the light detection device, and wherein the control unit processes an output signal of the light detection device, determines a hydrogen concentration, and delivers a respective signal.

According to a yet further aspect, the use of a thin film of an alloy in a hydrogen sensor is provided. The alloy comprises Mg, Ni, and M, wherein M is at least one of Zr, Ta, and Hf, and the alloy has the composition $Mg_xNi_yM_z$, wherein x is from 40 to 60, y is from 10 to 40, and z is from 10 to 40.

Further advantages, features, aspects and details that can be combined with embodiments described herein are evident from the dependent claims, the description and the drawings.

The provided optical sensor and detection system employing it, as well as the described methods for operation and uses thereof in electrical devices, all according to embodiments of the invention, allow for obtaining a good estimate of a condition of the electrical equipment and/or of its insulation liquid using a hardware setup that works reliably and needs only minimal calibration. Due to the optical detection, electrical interference can be avoided, and the system is intrinsically safe, due to the lack of electrical contacts and conductors in the sensing area. Further, the system uses cheap standard optical components, is therefore simple, cost-effective and robust, and does not have moving parts. It can be extended with many fiber sensors used simultaneously at same or different positions, which can thus be used to locate where a fault occurs, or to add redundancy cost-effectively and/or prevent false readings. The sensor assembly is especially advantageous for the monitoring of oil-filled transformers. A metal-alloy hydride system is provided in embodiments as a sensing layer which has a large optical change and an inclined pressure transmission isotherm in the temperature and pressure range of interest. Furthermore, the provided sensor and detection system are stable with respect to cycling and in time, in particular in the temperature range of particular interest, which is from at least about 5° C. to at least about 100° C.

BRIEF DESCRIPTION OF THE DRAWINGS

More details will be described in the following with reference to the figures, wherein.

DETAILED DESCRIPTION OF THE INVENTION

As used herein, metal alloys defined by a formula with atomic percentage values typically adding to 100 percent, such as, for example, $Mg_{52}Ni_{20}Zr_{28}$, are meant to also include substances with a composition deviating from that with the exact numbers provided. Typically, alloys having a composition wherein each number, independently from each other, has a tolerance of +/−15 percent, are still regarded to fall under the metal alloy provided by provision of the exact formula, such as the example above, also if the single numbers do not add up to 100 in total. Also, as used herein, such alloys may comprise further, non-named substances such as chemical elements of smaller amounts, such as up to about 2 percent each, but not more than about 10 percent in total.

As used herein, the term "fluid" is intended to be both representative for gases and liquids. It is, however, mainly used to be representative of an insulation liquid, particularly an oil, which is part of the insulation and/or cooling system of an electrical device, more particularly of a power transformer.

In the following, some aspects of the invention are described in detail. Aspects and parts of aspects are independent of each other and can be combined in any manner. For example, any aspect or embodiment described in this document can be combined with any other aspect or embodiment, as long as the combinations achieved are technically feasible.

First, some general possible aspects relating to the sensor assembly are described. The sensor assembly is adapted for sensing a status condition of an insulation-liquid-filled electrical equipment. Herein, electrical equipment refers to any equipment such as shunt reactors, bushings and transformers. The invention is particularly suited for the insulation liquid being insulation oil, be it on a mineral basis or from organic sources, such as palm oil. The invention is further particularly suited for the electrical equipment being a transformer, such as a power or distribution transformer, and more particularly for an oil-filled transformer.

The status condition of the electrical equipment is herein expressed by the hydrogen content (or hydrogen concentration) of the insulation liquid, which is a reliable indicator of various conditions, in particular fault conditions. The hydrogen content is defined as the amount of hydrogen dissolved in the insulation liquid (in ppm). A hydrogen sensitive layer (henceforth also called sensing layer) of an optical sensor is arranged in communication with the fluid (insulation liquid, oil), and is preferably immersed in the insulation liquid, so that the amount of hydrogen dissolved in the insulation liquid results in a characteristic partial pressure of hydrogen at the optical sensor, this partial pressure being a function of the hydrogen content (in ppm) in the insulation liquid. This relation may depend on additional parameters such as the temperature of the insulation liquid and/or of the hydrogen sensitive layer, and on the type of oil used in the transformer. Herein, the term "hydrogen" may refer to hydrogen molecules or atoms (which may be radicals). As used herein, the sensing layer "being in communication with a fluid" means that the gaseous components of interest present in the fluid, in particular hydrogen, may reach the sensing layer, even if other layers for catalysis, protection or the like are located between the sensing layer and the fluid. The metal alloy of the sensing layer reacts with this hydrogen from the fluid, which diffuses through a protection layer, and builds a metal-alloy hydride system. The latter reaction is a reason for the change in optical properties of the sensing layer when hydrogen is present, which is used for a hydrogen detection in embodiments.

Next, some aspects relating to the light source are described in more detail. Herein, light is defined as electromagnetic radiation. The radiation may have any wavelength, but is preferably in one of the mid-IR, near-IR, and visible wavelength ranges.

Next, some aspects relating to the optical sensor for detecting hydrogen are described in more detail. The optical sensor for detecting hydrogen is optically coupled to a light source for receiving light from the light source. The optical sensor has a sensing layer that changes its optical response with respect to the received light, in particular its reflectance, depending on an amount of hydrogen present in the sensing layer. This means, a changing hydrogen partial pressure also leads to a change in reflectance of the sensing layer. As the sensing layer is part of the optical sensor, the optical sensor also changes its reflectance.

As stated above, the amount of hydrogen can be defined in terms of a partial pressure of hydrogen at the optical sensor, which is directly related to an amount of hydrogen (in ppm) dissolved in the insulation liquid. Thereby, the reflectance of the optical sensor expresses the amount of hydrogen, and can therefore be taken as a status indicator of the electrical equipment—as a growing hydrogen concentration is an early indication for potential fault of the electrical equipment, as described further above. Thereby, from experience, thresholds for the hydrogen concentration are defined, which are herein regarded to be indicative for potential failure when exceeded. A first threshold is defined to be 150 ppm, and a second threshold is defined to be 250 ppm. These thresholds have, however, to be regarded as non-limiting examples only, and may be defined differently under differing operating conditions and setups without deviating from the scope of this disclosure.

The optical sensor and the hydrogen detection system employing the same are configured such that the sensing layer is immersed, during operation, in the insulation liquid of the electrical equipment. The optical response may include transmission, reflection, absorption and/or other properties detectable by typical light detection devices.

According to an aspect, the optical response is a reflection, and the optical sensor (more precisely, its sensing layer) is mounted (e.g. laminated or coated) to an end portion of a light guiding substrate coupling the optical sensor to the light source and to the light detection device (possibly via other optical conducting materials as well). In particular, the light guiding substrate is an optical fiber, wherein the sensing layer is coated to an end surface of a core of the optical fiber. Typically, the sensing layer is part of a multilayer structure, which also comprises a catalyst layer which includes Palladium (Pd). Further, auxiliary layers comprising Titanium (Ti) may be provided between the core of the optical fiber and the sensing layer, and between the sensing layer and the catalyst layer. Also, typically the outermost layer of the multilayer is a coating layer, which protects/shields the sensing layer and the catalyst layer from the insulation liquid, which is typically present in the form of an oil volume.

In aspects, the auxiliary layers of the multilayer may include an adhesion layer (or sticking layer) interposed between the sensing layer and the light guiding substrate, that is in particular the core of an optical fiber. Another auxiliary layer may be a separation layer between the catalyst layer and the sensing layer. The catalyst layer typically comprises a catalyst metal for splitting up hydrogen molecules from the insulation liquid, also called fluid herein, to single H atoms. E.g., the layer may comprise Pd or a Pd alloy, e.g. Pd—Au, Pd—Cu, Pd—Ag.

In aspects, the protection layer may be a PTFE coating, or a PMMA, $SiO_2$, Aluminum Oxide coating, or may be a multilayer structure comprising a combination of two or more layers each comprising one of the former materials. The protection layer may cover the catalyst layer and sensing layer on the optical sensor's insulation-liquid-facing side, preferably covering the entire insulation-liquid-facing side of the multilayer. The protection layer is typically permeable for hydrogen, but less permeable (or best: not permeable) with respect to at least some other components of the insulation liquid, e.g. other gases dissolved therein such as $O_2$, $H_2S$ and/or CO, and the liquid components of the insulation liquid/oil itself. The shielding effect is desirable, because some of these gases or oil components other than hydrogen might affect the detection accuracy of the optical sensor, or may influence and/or deteriorate their physical integrity and/or sensing and catalytic properties when in contact with the sensing layer or catalyst layer. In particular, permanent or reversible poisoning of the sensing layer with a gas other than the gas to be detected may negatively influence the detection accuracy.

In aspects, the sensing layer for hydrogen comprises a metal alloy that changes its optical response depending on the amount of hydrogen present in the fluid surrounding the optical sensor and thus also the sensing layer, hence typically the insulation liquid, in particular the oil used for insulation of an electrical device.

The optical sensor according to aspects, which includes a thin film of a metal alloy as a sensing layer, typically comprises a multimode optical fiber in combination with a fiber-tip micro-mirror configuration including that sensing layer. The micro mirror comprises the multilayer described earlier. In order to measure the hydrogen concentration in a continuous way, a single hydride forming metal as a sensing layer, like for example Pd or Mg, is not suited due to the metal-hydride phase transition at a single plateau pressure and temperature, or due to limited "pressure-transmission-isotherm" characteristics. Therefore, one needs to alloy the metal thin film with suited other metal(s) to obtain a pressure-transmission isotherm with non-negligible slope in the desired pressure and temperature range. By doping a Mg—Ni based alloy with a relatively large atom like Zr, Ta or Hf, the alloy becomes mainly amorphous, or at least shows the characteristics of an amorphous alloy: A group of these alloys according to embodiments show a well-defined relation between their optical response (e.g., reflectance) and the applied hydrogen partial pressure due to their amorphousness. It was found that for some particular alloys, the pressure-transmission isotherm has particularly useful characteristics in the hydrogen concentration and temperature range which is of interest for measuring hydrogen partial pressures in the insulation liquids of electrical equipment, in particular power transformers. It was found that with a Mg—Ni-M based alloy as a hydrogen sensing layer, wherein M is Zr, Ta, or Hf, it is possible to continuously monitor the hydrogen concentration in the oil of an operating power transformer, and thus to check for the condition of that power transformer. Thus, in embodiments, by using a single optical fiber based system—or even a multifiber based system—and an online, real time readout system, it is possible to check the status of the transformer at any moment and even localize possible defects. Also, it was found that in such embodiments, the Mg based complex metal hydrides may be covered with protective coatings including PMMA, PTFE, $SiO_2$, and Aluminum Oxide, in particular $Al_2O_3$.

In aspects, further examples for Mg alloys which may be used have different optical characteristics when used in an optical sensor are Mg compounds such as Mg—Ni compounds and Mg—Ti compounds, or Mg, V, Y or other compounds thereof. Particularly, Mg—Ni compounds showing this effect are $Mg_2Ni$. For example, $Mg_2Ni$ has a relatively high reflectivity, but under the influence of surrounding hydrogen at least a portion thereof is converted to $Mg_2NiH_4$, which is much less reflective at room temperature. However, these alloys, when used in a sensing layer as described further above, have different optical properties than the Mg—Ni-M alloys described previously, and are thus suitable for other, or partially overlapping, ranges of temperature and hydrogen partial pressures.

Making use of the phenomenon just described, in aspects at least two optical sensors may be combined in one hydrogen detection system, which each have an optimal working range with respect to a specific temperature and hydrogen partial pressure range of interest, and thus are used to complement each other in order to broaden the overall measurement range of the hydrogen detection system. Thus, in aspects a hydrogen detection system may comprise, in addition to the first optical sensor described above, a second optical sensor having a second sensing layer, that also changes its optical response (e.g. reflectance) with respect to the received light, depending on a hydrogen partial pressure in the fluid in contact with the sensing layer. Thereby, each of the two, or also three or more, optical sensors having differing sensing layers may be optically connected to a common light source, to its individual light source, and/or to a separate light detection section. Further, several identical optical sensors may be employed at different positions of a device in order to additionally obtain information about a location of a fault.

In the following, a (first) optical sensor and related aspects are described in more detail. A light detection device is optically coupled to the optical sensor comprising the multilayer with the sensing layer, the catalyst layer, one or more auxiliary layers and the protective layer, for receiving light having interacted with the sensing layer of the optical sensor. Thus, an amplitude (and/or optionally other properties, such as, e.g., phase and/or polarization) of the light received by the light detection device depends on the optical response of the sensing layer of the optical sensor. The light detection device produces an output signal S1 which is inputted into a control unit.

The control unit in aspects also receives a temperature signal from a temperature sensor, which measures the temperature of the fluid, which is the insulation liquid or oil, adjacent to the optical sensor. The temperature sensor may be closely integrated with the optical sensor, or may also be placed in a distance from it—in the latter case, it has to be assured that the temperature measured can be calculated in a defined relation to the temperature of the fluid at the optical sensor.

In aspects, the control unit may output a signal which is proportional to the amount of light received therein, which depends on the amount of hydrogen, or the partial pressure, in the surrounding fluid at the location of the optical sensor. Also, the control unit may output an analogous signal S2 which is proportional to the partial pressure measured.

According to aspects, the control unit comprises an input section for receiving a signal S1 from the light detection device, which detects the light from the light source after being reflected in the optical sensor. A signal analyser in the control unit serves for analysing the output signal of the light detection device. The light detection device may for example be a photo diode, a spectrum analyser, or other principally known devices suitable for analyzing the reflected light from the optical sensor. If polarization of the reflected light shall additionally be analyzed, also a polarizing filter or the like may be employed in the light detection device.

The control unit may comprise a visual output element, which is configured for displaying a signal depending on the detected hydrogen level. For example, the hydrogen level may be output on a numerical display having seven-segment displays, or on a monitor such as an LCD monitor. Also, the control unit may be configured to calculate a timely deviation of the hydrogen signal, and to display an alert, for example as a red light, when the deviation is positive or exceeding a boundary value, indicating a rise in hydrogen concentration, which is regarded as being caused by a fault in the electrical device such as the transformer which is monitored.

Further, the optical sensor may in aspects be accompanied by a thermostat unit, which is arranged for keeping a temperature of the first (and, if present, second, third, etc.) optical sensor within a predetermined temperature range. The heater may, e.g., be configured for being activated and/or deactivated periodically according to a temperature cycle, or may be adapted to keep a temperature of the optical sensor(s) within a predefined range. Thus, the sensor always works at the same temperature, which eliminates one variable (temperature) from the detection process, thereby potentially enabling higher detection precision.

According to aspects, an electrical equipment with an insulation liquid is provided, wherein the optical sensor described herein is immersed in the insulation liquid (i.e. partially immersed so that the optical sensor is at least in partial contact with the insulation liquid).

Figure 1:
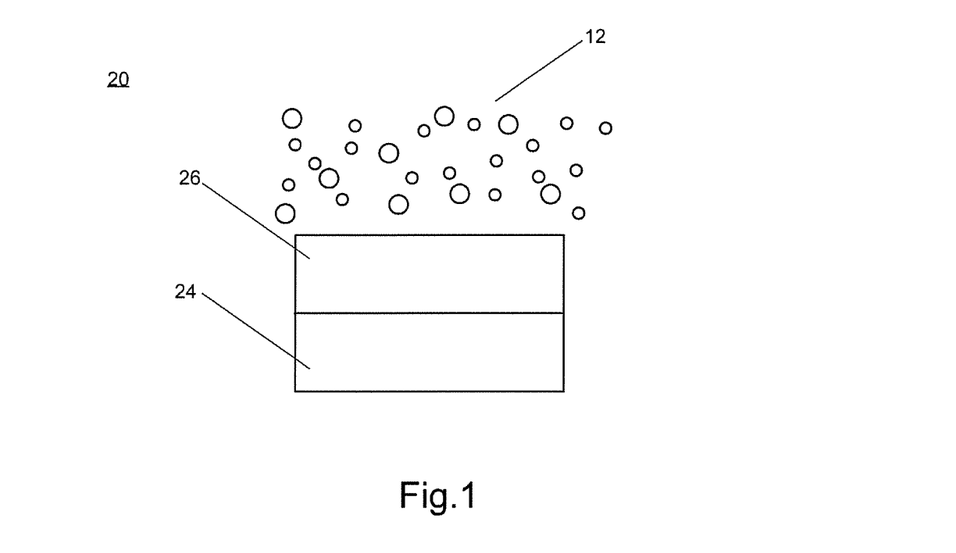
FIG. 1 is a schematic view of a multilayer of an optical sensor according to embodiments.

FIG. 1 shows a multilayer 20 of an optical sensor 10 according to embodiments. The multilayer 20 comprises a sensing layer 24, which is composed of a metal alloy. The alloy comprises Mg, Ni, and a component M, wherein M is at least one of Zr, Ta, and Hf. The alloy has the composition $Mg_xNi_yM_z$, wherein x is from 40 to 60, y is from 10 to 40, and z is from 10 to 40, in combinations where the numbers add up to 100. The catalyst layer 26 comprises Pd or a Pd alloy. In between the catalyst layer 26 and the sensing layer 24, an auxiliary layer (not shown, see FIG. 3) is typically provided in embodiments in order to physically separate the two layers and to block atoms from either layer to wander due to diffusion into the other layer, which would be undesirable. This blocking effect might also be carried out by a surface treatment prior to the provision of the catalyst layer on the sensing layer, which was however not tested.

Figure 2:
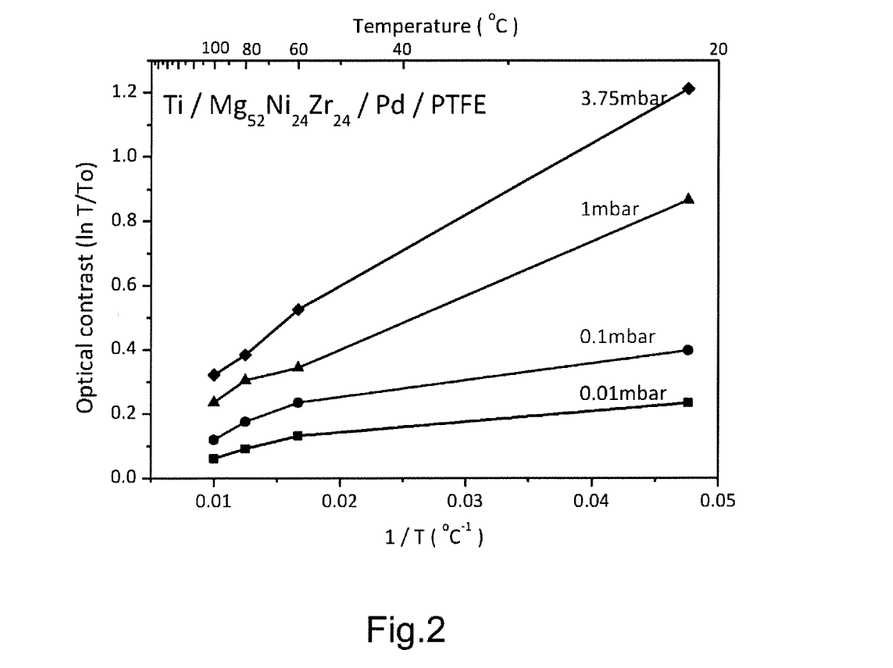
FIG. 2 is a schematic view of a sensor characteristic according to embodiments.

In embodiments, the multilayer 20 comprises a sensing layer with one of the alloys with the basic composition $Mg_{52}Ni_{20}Zr_{28}$ and $Mg_{55}Ni_{27}Ta_{18}$, wherein the individual amount of the components may deviate by +−15%. In FIG. 2, the logarithm of the normalized transmission for light of a wavelength 635 nm of a multilayer as shown in FIG. 1 is depicted, wherein the catalyst layer comprises Pd, and the sensing layer comprises $Mg_{52}Ni_{24}Zr_{24}$, according to embodiments. Thereby, the logarithm of the transmission is drawn over the inverse temperature. A well-defined temperature dependence is observed, i.e. for an increasing temperature the optical contrast decreases. As a first approximation, the optical response can be described by an inverse linear dependence of temperature for a certain hydrogen partial pressure. Moreover, there is an almost directly proportional relation between the logarithm of the transmission—with respect to a reference reflectance $T_0$—over a temperature range from 100° C. (1/T=0.01° C.$^{-1}$) and room temperature 20° C. (1/T=0.05° C.$^{-1}$). In this temperature range, there is also a significant variation of the optical contrast in dependence of the hydrogen partial pressure, expressed by the contrast difference between the drawn exemplary graphs for 0.01 mbar hydrogen partial pressure, 0.1 mbar, 1 mbar, and 3.75 mbar. According to findings of the inventors, the partial pressure of 0.01 mbar corresponds to a hydrogen concentration of about 0.6 ppm at 60° C. in oil. Thus, an optical sensor with the sensing layer having the above properties is able to at least detect a hydrogen concentration as small as 0.6 ppm. This is well below a threshold hydrogen level in oil which is known to indicate a potential or developing fault in a transformer insulation, which may be defined as 100 ppm or 150 ppm, as non-limiting examples only. The depicted graphs, and further data to fill the gaps between the graphs depicted, is in embodiments stored in a look-up table of a control unit, so that a hydrogen partial pressure may be determined in real time from the measured reflectance of the optical sensor comprising such a substrate, and a measured temperature of the optical sensor or in the vicinity of that optical sensor.

Figure 3:
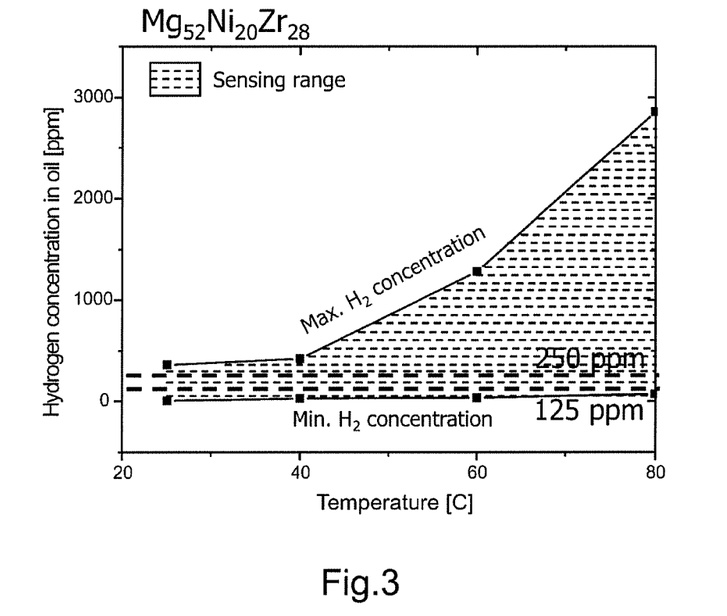
FIG. 3 is a further schematic view of a sensor characteristic according to embodiments.

FIG. 3 shows that with an optical sensor according to embodiments, having a multilayer 20 with a Pd-comprising catalyst layer 26 and a sensing layer 24 comprising $Mg_{52}Ni_{20}Zr_{28}$, it is possible to measure the hydrogen concentration in transformer oil from 25 ppm to 290 ppm at 21° C. More importantly, at higher temperatures which are closer to standard operating temperatures of transformers, the sensing range reaches from 30 ppm to 2500 ppm at 60° C. in a continuous manner. The sensing range reaches further up to 80° C., which is already beyond a standard operating temperature of power transformers. Therefore, at room temperature, this optical sensor already covers the above named threshold of interest for transformer fault detection of 150 ppm, and at 60° C. it covers the entire sensing range of interest for transformer monitoring.

Figure 4:
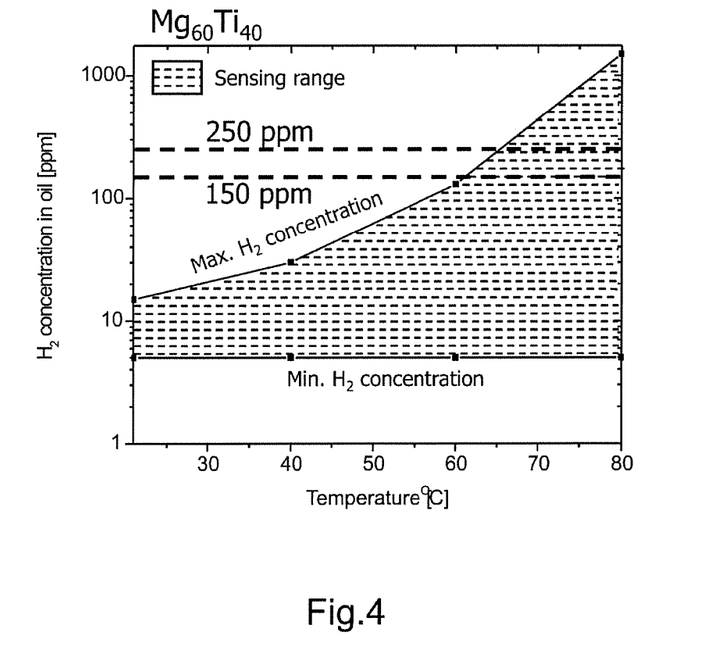
FIG. 4 is a schematic view of a sensor characteristic of a known sensor.
Figure 5:
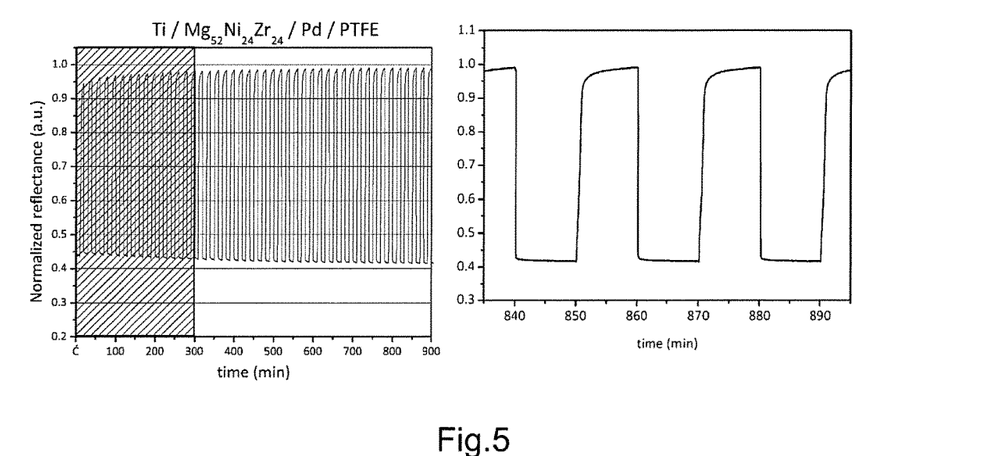
FIG. 5 is a diagram of a graph of an operation of an optical sensor according to embodiments.

In FIG. 4, as a comparison, the sensing range for a similar multilayer 20 is depicted, which comprises a sensing layer 24 comprising a previously known $Mg_{60}Ti_{40}$ alloy sensing layer 24. As can be seen, the threshold value of interest, 150 ppm, can only be detected from about 60° C. upwards with an optical sensor having such a sensing layer. Below that temperature, the multilayer 20 does not show a significant change in optical response (in comparison to 0 ppm concentration) which would be suitable for detection.

Alternatively, respectively in addition, a Pd-catalyst layer 26 capping a sensing layer 24 with an alloy of $Mg_{55}Ni_{27}Ta_{18}$ is also able to measure the dissolved hydrogen in oil in the same concentration range as the $Mg_{52}Ni_{20}Zr_{28}$ based sensor as shown in FIG. 3. However, for the same hydrogen concentration, the change in reflection of the $Mg_{55}Ni_{27}Ta_{18}$ based alloy is smaller than the change exhibited by the Pd-capped $Mg_{52}Ni_{20}Zr_{28}$ sensor. This results in a lower signal to noise ratio. Therefore, optical sensors with $Mg_{52}Ni_{20}Zr_{28}$ sensing layers 24 seem slightly advantageous over a $Mg_{55}Ni_{27}Ta_{18}$/Pd based optical sensor.

Both the described examples for sensing layers according to embodiments, $Mg_{52}Ni_{20}Zr_{28}$ and the $Mg_{55}Ni_{27}Ta_{18}$ sensing layers 24, in combination with Pd catalyst layers 26, show a highly reproducible optical response upon cycling, after being pre-cycled 15 times. Precycling was done by performing a hydrogen absorption-desorption cycle with a 4% $H_2$ in Argon flow in the gas phase at room temperature, wherein this cycle was repeated 15 times. It was found that the pre-cycling is positively influencing a stable optical response of the optical sensor afterwards. XRD measurements indicated that cycling does not affect the amorphous microstructure of the sensing layer, and AFM pictures confirmed that cycling does not result in buckling, delamination, or a large microstructural change of a $Mg_{52}Ni_{20}Zr_{28}$ thin film. The typical response time of optical sensors with multilayers 20 with sensing layers 26 as described above is, when immersed in transformer oil, within the range of hours. Thereby, the actual response time depends strongly on the hydrogen concentration in the oil.

Figure 6:
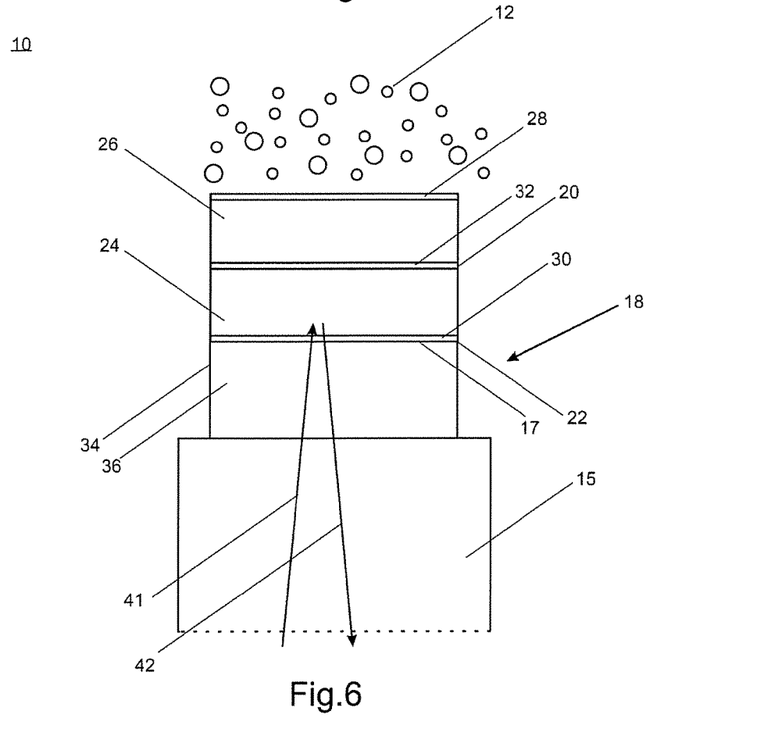
FIG. 6 is a schematic view of an optical sensor according to embodiments.

In FIG. 6, an optical sensor 10 according to embodiments is shown, comprising a multilayer 20 as described above, with a sensing layer 24 and a catalyst layer 26. The optical sensor 10 is suitable for detecting hydrogen in a fluid 12 (schematically shown, with smaller circles representing dissolved hydrogen in the fluid) which is in physical contact with the optical sensor 10. The multilayer is coated to an end portion 18 of an optical fiber 15. The latter typically has an outer diameter, including cladding and coating, of about 230 μm, the core 36 has about 200 μm diameter. It is understood that also significantly different fiber diameters are applicable. The sensing layer 24 comprises a film of an alloy, wherein the alloy of the sensing layer may have the compositions which were described above with respect to FIG. 1 to FIG. 4. The catalyst layer 26 comprises Pd or a Pd alloy. The catalyst layer 26 is coated with a coating layer 28. The coating layer typically comprises PMMA and/or PTFE and/or $SiO_2$ and/or Aluminum Oxide, such as $Al_2O_3$. Also, the coating layer 28 may have a multilayer structure, comprising at least two or more layers of PMMA, PTFE, $SiO_2$ and Aluminium Oxide. It protects the catalyst layer and sensing layer from the oil or other fluid, and blocks unwanted gases dissolved in the fluid from reaching the sensing layer, such as CO or $H_2S$. PTFE may in embodiments be chosen as the outermost coating layer (if several layers are present) in order to shield from the oil components.

As was laid out with respect to FIGS. 2 and 3, the optical sensor 10 exhibits a continuous decrease of the optical reflectivity in the visible optical range when exposed to a growing hydrogen concentration (measured in ppm) in a fluid 12 in contact with the optical sensor 10. For suitable sensing layers according to embodiments, the optical sensor 10 shows a continuous dependency of its optical reflectance from the hydrogen concentration in a range from about 5° C. to about 150° C., and for hydrogen concentrations in the fluid from about 0.5 ppm to about 5000 ppm, more particularly from about 2 ppm to about 3000 ppm.

The optical sensor 10 of FIG. 6 comprises an auxiliary layer 32 between the catalyst layer 26 and the sensing layer 24, which abuts the sensing layer 24. The auxiliary layer 30 preferably comprises Ti, which is suitable to block atoms from either neighbouring layer to diffuse into the respective other layer. A further auxiliary layer 30, also typically comprising Ti, is provided as an adhesive layer between the core 36 of the optical fiber 15 and the sensing layer 24. In embodiments, the coating layer reaches over the entire multilayer 20, that is, also over the circumferential side faces of the multilayer 20 (not shown).

The multilayer 20 is typically provided on an end surface 17 of the optical fiber 15, perpendicular to the longitudinal axis of the optical fiber. In embodiments, most or all layers of the multilayer 20 overlap over the edge 22 of the core 36 to cover a portion of the circumferential side face 34 of the core 36 of the optical fiber 15. In embodiments, the multilayer may also be provided exclusively on the peripheral side face 34 of the core optical fiber 15. Also, the multilayer 20 may in embodiments be provided on an optically transparent substrate (not shown) different from an optical fiber.

In all embodiments, typical dimensions (i.e., a thickness parallel to the longitudinal axis of the optical fiber) for the varying layers of the multilayer 20 are: Auxiliary layers from 2 to 7 nm, more typically from 4 to 6 nm, for example 5 nm. The sensing layer is typically from 30 to 80 nm, more typically from 40 to 70 nm, for example 60 nm thick. The catalyst layer 26 is typically from 15 nm to 50 nm, more typically from 20 to 40 nm, for example 30 nm thick. The thickness of the coating layer may vary depending on its individual setup, in particular if it comprises several layers of differing materials, as described herein. It may thus have a thickness from 3 nm to 5 μm, more typically from 20 nm to 3 μm, for example 1 μm or 2 μm. It shall also be noted that the proportions in the figures are not to scale. For example, the optical fiber 15 in FIG. 6 has a diameter of about 230 μm, whereas the individual layers are in the range from a few nm up to a few μm, as just described. Thus, their height or thickness (in a vertical direction in the drawing plane) is significantly smaller, in reality, in relation to the horizontal dimension of the fiber.

Schematically, an incoming light beam 41 is shown, which is reflected in the sensing layer 24 and mirrored back into the optical fiber 15 as light beam 42. The optical fiber 15 is typically a multimode fiber, the wavelength may for example be about 635 nm, but also any other wavelength in the visible optical range is applicable with the sensing layers 24 as described herein. The exact position at which the light is reflected in the sensing layer in FIG. 6 is randomly chosen for illustrational purposes only.

Figure 7:
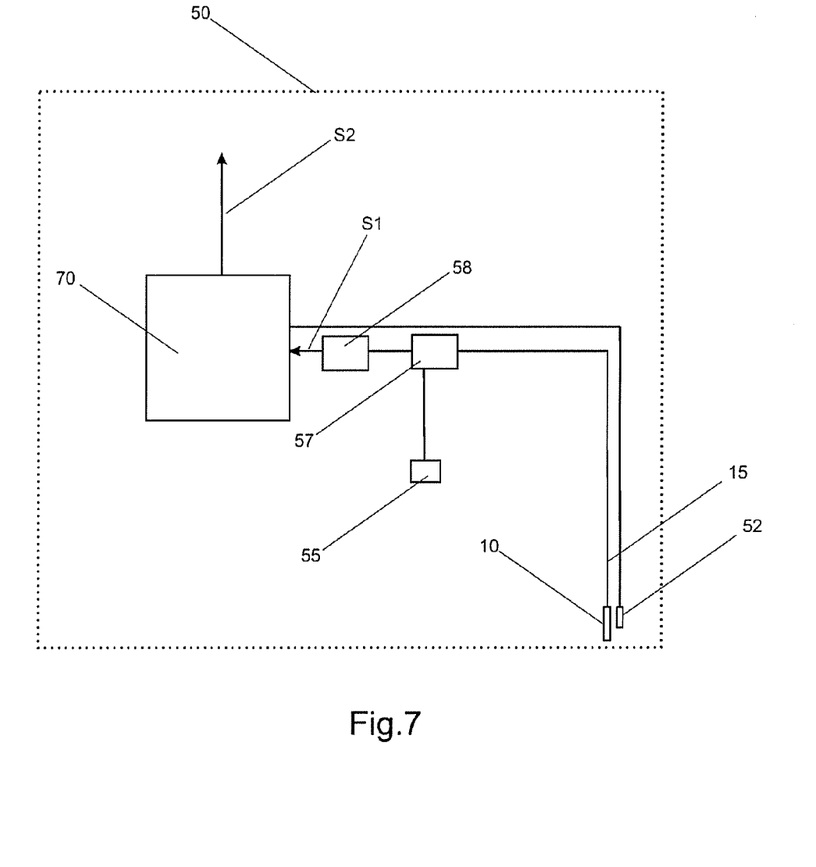
FIG. 7 is a schematic view of a detection system according to embodiments.

In FIG. 7, a detection system 50 for hydrogen in fluids is shown. It comprises the optical sensor 10 as described above. Further, it comprises a temperature sensor 52, a light source 55, a light detection device 58, an optical splitter 57, and a control unit 70. Light from the light source 55 is coupled by the splitter 57 into the optical sensor 10. In the optical sensor 10, the sensing layer 24 of the multilayer 20 (both not shown) reflects a portion of the incoming light. The reflected light reflects back through the splitter 57 and is detected by light detection device 58. The latter produces an output signal S1 depending on the amplitude of the reflected light received. The control unit 70 processes the output signal S1 of the light detection device 58. It determines a hydrogen concentration and delivers a respective output signal S2. Thereby, it takes into account temperature T delivered from temperature sensor 52. Thereby, the control unit 70 makes use of data stored in a look-up table. The stored data comprises characteristic reflectance data of the optical sensor 10 for a variety of temperatures (in the range of interest, e.g. 10° C. to 100° C.) and a variety of partial pressures of hydrogen in a fluid 12 (not shown) surrounding the optical sensor 10. Thus, the detection system 50 provides an output signal S2 depending on the calculated hydrogen concentration in the fluid 12, which is calculated from the measured values for temperature and reflectance. Signal S2 is determined from the reflectance of the optical sensor 10 and the temperature. Thereby, the output signal S2 in embodiments is typically a continuous function of the hydrogen concentration in the fluid 12. The detection system typically delivers a continuous decrease of the output signal S2 in a temperature region between 5° C. and 150° C., and for hydrogen concentrations in the fluid 12 from about 0.5 ppm to about 5,000 ppm, more typically from about 2 ppm to about 3000 ppm.

Alternatively to the use of a look-up table, the hydrogen concentration may be calculated by the control unit 70 from a stored function set, taking into account at least the parameters reflectivity of the optical sensor 10 and the temperature from the temperature sensor 52.

It is understood that the described optical sensors 10 and detection systems have to be characterized prior to their use in order to obtain the data mentioned above about the relation between hydrogen partial pressure, temperature and reflectance of the optical sensor. As such optical sensors can be reproduced with high precision, this might only be necessary for a prototype. The obtained data then may be reused in the mass production process.

Figure 8:
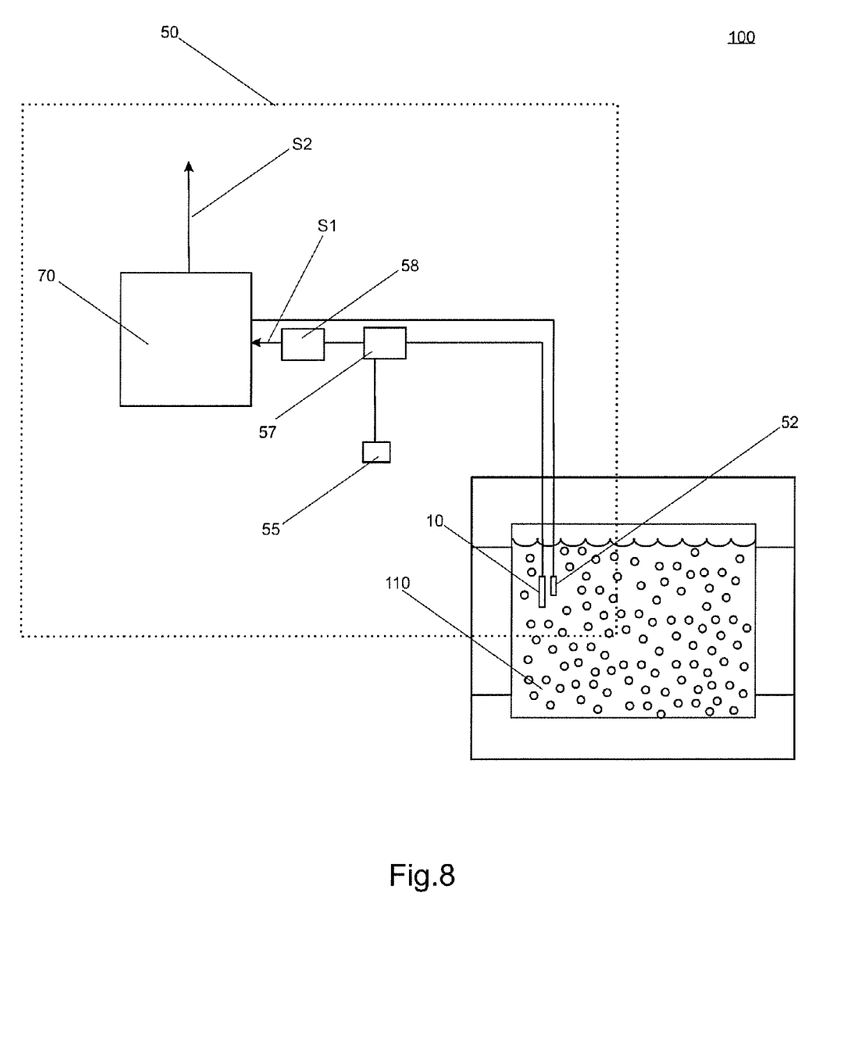
FIG. 8 is a schematic view of an electrical device according to embodiments.

In FIG. 8, an electrical device 100 is shown. It includes a hydrogen detection system 50 as described with respect to FIG. 7. The device 100 is generally a device for electric power generation, transmission, or distribution, and more typically a power transformer or distribution transformer. It comprises an oil volume 110 for insulation and cooling purposes, in which the optical sensor 10 and the temperature sensor 52 are immersed. More precisely, the end portion 18, with the multilayer 20, of the optical fiber 15 is immersed in the oil volume 110. The temperature sensor 52 is provided to measure the temperature of the oil directly at, or adjacent to the multilayer 20 of the optical sensor 10. The oil is representative of the fluid 12 shown in other figures herein.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. While various specific embodiments have been disclosed in the foregoing, those skilled in the art will recognize that the spirit and scope of the claims allows for equally effective modifications. Especially, mutually non-exclusive features of the embodiments described above may be combined with each other. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. An optical sensor for detecting hydrogen in a fluid in physical contact with the optical sensor, the optical sensor comprising:
an optical fiber, wherein an end portion of the optical fiber is coated with a multilayer including:
a sensing layer, including a film of an alloy, the alloy including Mg, Ni, and M, wherein M is at least one of Zr, Ta, and Hf, and wherein the alloy has the composition $Mg_xNi_yM_z$, and wherein x is from 40 to 60, y is from 10 to 40, and z is from 10 to 40; and
a catalyst layer including Pd.

2. The optical sensor of claim 1, wherein the alloy includes at least one of $Mg_{52}Ni_{20}Zr_{28}$, $Mg_{52}Ni_{24}Zr_{24}$, and $Mg_{55}Ni_{27}Ta_{18}$.

3. The optical sensor of claim 1, wherein the multilayer includes the sensing layer, the catalyst layer, and a coating layer.

4. The optical sensor of claim 3, wherein the coating layer includes PMMA and/or PTFE and/or $SiO_2$ and/or Aluminum Oxide, or has a multilayer structure including at least two of PMMA, PTFE, $SiO_2$, and Aluminum Oxide.

5. The optical sensor of claim 1, wherein the optical fiber is configured such that the optical sensor exhibits a continuous decrease of optical reflectivity in a visible optical range in dependency of a growing hydrogen partial pressure in a fluid in contact with the optical sensor.

6. The optical sensor of claim 5, wherein the continuous decrease occurs in a temperature region between 5° C. and 150° C. and for a hydrogen partial pressure between 0.5 ppm and 5,000 ppm.

7. The optical sensor of claim 1, wherein the optical fiber further includes at least one auxiliary layer abutting the sensing layer, the auxiliary layer including Ti.

8. The optical sensor of claim 1, wherein the multilayer is provided on an end surface of the optical fiber perpendicular to a longitudinal axis of the optical fiber.

9. A detection system for hydrogen in a fluid, comprising:
an optical sensor including:
an optical fiber, wherein an end portion of the optical fiber is coated with a multilayer including:
a sensing layer, including a film of an alloy, the alloy including Mg, Ni, and M, wherein M is at least one of Zr, Ta, and Hf, and wherein the alloy has the composition $Mg_xNi_yM_z$, and wherein x is from 40 to 60, y is from 10 to 40, and z is from 10 to 40; and
a catalyst layer including Pd;
a temperature sensor;
a light source;
a light detection device; and
a control unit;
wherein light from the light source is coupled into the optical sensor, and light reflected by the multilayer of the optical sensor is detected by the light detection device; and
wherein the control unit processes an output signal "S1" of the light detection device, determines a hydrogen concentration, and delivers a respective output signal "S2".

10. The detection system of claim 9, wherein the control unit is configured to provide an output signal "S2" depending on the hydrogen concentration determined from a reflectivity of the optical sensor and a temperature; and
wherein the output signal "S2" is a continuous function of the hydrogen concentration in the fluid.

11. The detection system of claim 10, wherein the control unit is configured to deliver a continuous change of the output signal "S2" in a temperature region between 5° C. and 150° C. and for a hydrogen partial pressure in the fluid between 0.5 ppm and 5,000 ppm.

12. The detection system of claim 9, wherein the control unit is configured to determine the hydrogen concentration by looking up stored data about a reflectivity of the optical sensor at various hydrogen partial pressures and temperatures, and/or to determine the hydrogen concentration from a stored function set, taking into account at least a reflectivity of the optical sensor and a temperature.

13. The detection system of claim 9, wherein the end portion of the optical fiber is immersed in an oil volume; and
wherein the temperature sensor is provided to measure a temperature of the oil volume at a position adjacent to the multilayer of the optical sensor.

14. A hydrogen sensor, comprising:
an alloy including Mg, Ni, and IA wherein M is at least one of Zr, Ta, and Hf, and wherein the alloy has the composition $Mg_xNi_yM_z$, and wherein x is from 40 to 60, y is from 10 to 40, and z is from 10 to 40.

15. The optical sensor as claimed in claim 8, wherein the multilayer overlaps over an edge of the optical fiber to cover a portion of a circumferential side face of a core of the optical fiber.

* * * * *